United States Patent
Lee et al.

(10) Patent No.: US 11,478,000 B2
(45) Date of Patent: Oct. 25, 2022

(54) COMPOSITION CONTAINING TWO LACTIC ACID BACTERIA STRAINS AND USES THEREOF

(71) Applicant: SYNBIO TECH INC., Kaohsiung (TW)

(72) Inventors: Ting-Yu Lee, Tainan (TW); Jin-Seng Lin, Tainan (TW)

(73) Assignee: SYNBIO TECH INC., Kaohsiung (TW)

(*) Notice: Subject to any disclaimer, the term of this patent is extended or adjusted under 35 U.S.C. 154(b) by 3 days.

(21) Appl. No.: 16/616,349

(22) PCT Filed: Aug. 23, 2019

(86) PCT No.: PCT/IB2019/057097
§ 371 (c)(1),
(2) Date: Nov. 22, 2019

(87) PCT Pub. No.: WO2020/250026
PCT Pub. Date: Dec. 17, 2020

(65) Prior Publication Data
US 2022/0000145 A1 Jan. 6, 2022

(30) Foreign Application Priority Data
Jun. 10, 2019 (TW) ................. 108119935

(51) Int. Cl.
| | | |
|---|---|---|
| *A23K 10/18* | (2016.01) | |
| *A23K 50/60* | (2016.01) | |
| *A61K 35/744* | (2015.01) | |
| *A61K 35/747* | (2015.01) | |
| *A23K 50/30* | (2016.01) | |
| *C12N 1/20* | (2006.01) | |
| *A61K 9/00* | (2006.01) | |
| *C12R 1/25* | (2006.01) | |
| *C12R 1/46* | (2006.01) | |
| *A61K 35/00* | (2006.01) | |

(52) U.S. Cl.
CPC ............. *A23K 10/18* (2016.05); *A23K 50/30* (2016.05); *A23K 50/60* (2016.05); *A61K 9/0056* (2013.01); *A61K 35/744* (2013.01); *A61K 35/747* (2013.01); *C12N 1/205* (2021.05); *A23Y 2220/67* (2013.01); *A23Y 2240/75* (2013.01); *A61K 2035/115* (2013.01); *C12R 2001/25* (2021.05); *C12R 2001/46* (2021.05)

(58) Field of Classification Search
CPC ........ A23K 10/18; A23K 50/30; A23K 50/60; A61K 9/0056; A61K 35/744; A61K 35/747; A61K 2035/115; C12N 1/205; C12N 1/20; A23Y 2220/67; A23Y 2240/75; C12R 2001/25; C12R 2001/46
See application file for complete search history.

(56) References Cited

PUBLICATIONS

Yerlikaya O. et al., "Production of probiotic fresh white cheese using co-culture with *Streptococcus thermophilus*", Food Sci. Technol., Campinas, vol. 34, No. 3, pp. 471-477 (Jul.-Sep. 2014). (Year: 2014).*
CN101940267A—published dated Jan. 12, 2011—Partial English machine translation by USPTO STIC for Chinese (FOR) patent; attached document with a total pp. 1-12. (Year: 2011).*
CN109122564A—published dated Jan. 4, 2019—Partial English machine translation by USPTO-STIC for Chinese (FOR) patent; attached document with a total pp. 1-17. (Year: 2019).*

* cited by examiner

*Primary Examiner* — Satyendra K Singh
(74) *Attorney, Agent, or Firm* — Hamre, Schumann, Mueller & Larson, P.C.

(57) ABSTRACT

Disclosed herein is a composition that includes *Lactobacillus plantarum* LP28 deposited at the China General Microbiological Culture Collection Center (CGMCC) under an accession number CGMCC 3346, and *Streptococcus thermophilus* ST30 deposited at Deutsche Sammlung von Mikroorganismen und Zellkulturen GmbH under an accession number DSM 32788. Also disclosed herein are an animal feed comprising the composition, and a method for improving pork quality, which comprises administering to a pig the composition.

4 Claims, No Drawings

COMPOSITION CONTAINING TWO LACTIC ACID BACTERIA STRAINS AND USES THEREOF

FIELD

The present disclosure relates to a composition and a method for improving pork quality. In particular, two lactic acid strains, namely *Lactobacillus plantarum* LP28 and *Streptococcus thermophilus* ST30, are used to upgrade the color, tenderness and marbling of the pork, wherein *Lactobacillus plantarum* LP28 is deposited at the China General Microbiological Culture Collection Center (CGMCC) under an accession number CGMCC 3346, and *Streptococcus thermophilus* ST30 is deposited at Deutsche Sammlung von Mikroorganismen und Zellkulturen GmbH under an accession number DSM 32788.

BACKGROUND

Feed additives are commonly used to improve the growth performance, livability, cumulative weight gain or feed efficiency in pigs as well as to enhance the meat quality in pigs. Feed additives are generally divided into seven main classes: (1) antibacterial agents, such as apramycin, carbadox, dimetridazole, roxarsone, sulfamethazine, amoxicillin, colistin, and tylosin; (2) antiparasitic agents, such as amprolium, ethopabate, nicarbazin, clopidol, cyromazine, monensin, and sulfaquinoxaline; (3) beta-adrenergic agonists, such as ractopamine, colterol, zipaterol, cimaterol, salbutamol, tulobuterol, terbutaline, andclenbuterol; (4) minerals, such as chromium, selenium, manganese, and magnesium; (5) ω-6 unsaturated fatty acids, such as conjugated linoleic acid; (6) alkaloids, such as betaine; and (7) vitamins, such as vitamin E. However, most of these feed additives are chemosynthetic materials, which may lead to higher production cost. Further, it is known that excess antibiotics and chemicals including those that are not metabolizable by animals may remain in the body, and thus may accumulate in the meat which will be consumed by humans and may cause harmful effects on the human body. Therefore, researchers in this field have attempted to develop safe and cost-effective feed additives to improve the meat quality in pigs.

Lactic acid bacteria (LAB) are gram-positive bacteria that produce lactic acid as the major metabolic end product of carbohydrate fermentation. These bacteria, which are usually found in pickled food, dairy products, and intestinal tract mucosa of animals, share common physiological characteristics, including being rod-shaped (bacilli) or spherical (cocci), catalase-negative, devoid of cytochrome, non-sporulating and non-motile.

LAB are conferred with the generally recognized as safe (GRAS) status, and are widely used as probiotics. Common LAB includes *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc. LAB have been shown to be capable of inhibiting the growth of pathogenic bacteria in the gastrointestinal tract and alleviating lactose intolerance, and have immunoregulatory, anticancer and blood pressure lowering effects.

In a number of studies, LAB strains have been intended to improve the meat quality in pigs. For example, CN 102356816 B discloses a probiotic fermentation starter for animal dietary supplement which can improve meat quality, and which comprises components A, B and C, wherein component A is a composition containing *Lactobacillus plantarum* and *Enterococcus faecalis*, component B is a composition containing *Lactobacillus acidophilus* and *Bifidobacterium*, and component C is *Saccharomyces cerevisiae*. In Examples 1 and 2 of CN 102356816 B, the probiotic fermentation starter was added to MRS medium, followed by conducting anaerobic fermentation at 35° C. for 36 hours, so as to obtain a probiotic liquid. The probiotic liquid could be further mixed with a complete feed, so as to obtain a fermented feed. The probiotic liquid and the fermented feed thus obtained were respectively fed to Landrace pigs (70-78 days old), and after a feeding time of 82-86 days, the pigs (156-160 days old) were slaughtered and the longissimus muscles were taken out for the evaluation of pork quality. Experimental results showed that the probiotic liquid and the fermented feed were able to improve juiciness and flavor in meat, but provided no effect on tenderness.

In developing a feed additive containing probiotics, the applicant has unexpectedly found that a composition comprising *Lactobacillus plantarum* LP28 with Accession No. CGMCC 3346 and *Streptococcus thermophilus* ST30 with Accession No. DSM 32788 can be used as a feed additive for improving color, tenderness, and marbling of the pork.

SUMMARY

Accordingly, in a first aspect, the present disclosure provides a composition for improving pork quality, which includes *Lactobacillus plantarum* LP28 deposited at the China General Microbiological Culture Collection Center (CGMCC) under an accession number CGMCC 3346, and *Streptococcus thermophilus* ST30 deposited at Deutsche Sammlung von Mikroorganismen und Zellkulturen GmbH under an accession number DSM 32788.

In a second aspect, the present disclosure provides an animal feed including a composition as described above.

In a third aspect, the present disclosure provides a method for improving pork quality, which includes administering to a pig a composition as described above.

DETAILED DESCRIPTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

Through research, the applicant suprisingly found that supplementing standard pig diets with a combination of particular lactic acid bacteria (LAB) strains results in a significant improvement of the pork quality including color, marbling, and tenderness.

Therefore, the present disclosure provides a composition for improving pork quality, which includes *Lactobacillus plantarum* LP28 deposited at the China General Microbiological Culture Collection Center (CGMCC) under an accession number CGMCC 3346, and *Streptococcus thermophi-*

*lus* ST30 deposited at Deutsche Sammlung von Mikroorganismen und Zellkulturen GmbH under an accession number DSM 32788.

As used herein, the term "pork quality" refers to the color, marbling, and tenderness of pork.

According to the present disclosure, *Lactobacillus plantarum* LP28 and *Streptococcus thermophilus* ST30 may be concentrated or non-concentrated, a liquid, a paste, a semi-solid, or a solid (e.g. a pellet, a granule, or a powder), and may be frozen, dried, or freeze-dried (for example, may be in freeze-dried form or spray/fluid bed dried form). In an exemplary embodiment, *Lactobacillus plantarum* LP28 and *Streptococcus thermophilus* ST30 are in freeze-dried powder form.

According to the present disclosure, *Lactobacillus plantarum* LP28 and *Streptococcus thermophilus* ST30 in the composition are present in a weight ratio ranging from 1:1 to 1.8:1. In an exemplary embodiment, the weight ratio of *Lactobacillus plantarum* LP28 and *Streptococcus thermophilus* ST30 is 1.8:1.

According to the present disclosure, the composition may have a total bacterial concentration ranging from $10^8$ colony-forming unit (CFU)/g to $10^{12}$ CFU/g. In an exemplary embodiment, the composition has a total bacterial concentration ranging from $10^{11}$ CFU/g to $10^{12}$ CFU/g.

According to the present disclosure, the composition may be admixed with one or more carriers, including, but not limited to: a solvent, a buffer, an emulsifier, a suspending agent, a decomposer, a dispersing agent, a binding agent, an excipient (e.g., maltodextrin, montmorillonite, whey, and calcium carbonate), a stabilizing agent, a chelating agent, a diluent, a gelling agent, a wetting agent, an absorption delaying agent, a liposome, and the like. The choice and amount of the aforesaid carriers are within the expertise and the routine skills of those skilled in the art. In an exemplary embodiment, the carrier used is maltodextrin.

In addition, the composition according to the present invention is expected to be used as a feed additive for improving pork quality. Therefore, the present disclosure provides an animal feed including the composition described above.

As used herein, the terms "feed additive", "complementary feed mix", or "feed supplement" are used interchangeably, and refer to an ingredient or a mixture or combination of ingredients which can be mixed to a feed to fulfill one or more specific need(s).

As used herein, the term "feed" refers to any kind of material, liquid or solid, which is used for nourishing an animal, and for sustaining normal or accelerated growth of an animal including newborns and young developing animals. In certain embodiments, the animal feed is a pig feed. In other embodiments, the animal feed may be a feed suitable for various animals including pigs.

According to the present disclosure, the composition may be incorporated into a pig feed using a standard technique well known to one of ordinary skill in the art. For instance, the aforesaid two LAB strains may be directly added to a pig feed, or may be utilized for preparing an intermediate composition (e.g., a feed additive or a premix) suitable to be subsequently added to a pig feed. In an exemplary embodiment, the pig feed is prepared by forming a feed additive containing the composition, and by mixing the feed additive with a basal diet.

According to the present disclosure, the feed additive may be mixed with the basal diet in a weight ratio ranging from 1:2000 to 1:10000. In an exemplary embodiment, the feed additive and the basal diet are mixed in a weight ratio of 1:5000.

According to the present disclosure, the animal feed can be prepared in any form suitable for oral administration, including, but not limited to: a liquid, a solid (e.g. a powder, a granule, a particulate, a compressed tablet), gel, slurry, etc. In an exemplary embodiment, the animal feed serving as a pig feed is in solid form. In another embodiment, the animal feed serving as a pig feed is in powder form.

The animal feed according to the present disclosure may further comprise at least one probiotic microbe. As used herein, the terms "probiotic microbe" and "probiotic" are used interchangeably, and refer to preparations of live microorganisms. These microorganisms may remain and survive in the gastrointestinal tract after ingested by an animal, and can exert a desired effect (e.g. gut microbiota modifying effect, preventive or therapeutic effect, etc.).

Probiotic microorganisms suitable for use in the present disclosure include, but are not limited to, *Lactobacillus* sp., *Lactococcus* sp., *Leuconostoc* sp., *Enterococcus* sp., *Streptococcus* sp., *Pediococcus* sp., *Bacillus* sp., *Bifidobacterium* sp., yeasts, and their combinations.

The feeding amount and frequency of the animal feed according to the present invention may vary depending on the following factors: the weight, age, physical condition and response of the animal to be fed. For instance, the daily amount of the animal feed according to the present invention may be 25 to 42 g/Kg body weight, and may be fed in a single amount or in several amounts.

According to the present disclosure, when the animal to be fed is a piglet, which has a body weight less than 30 Kg, the daily amount of the animal feed is 40 g/Kg body weight.

According to the present disclosure, when the animal to be fed is a growing pig, which has a body weight between 30 and 60 Kg, the daily amount of the animal feed is 42 g/Kg body weight.

According to the present disclosure, when the animal to be fed is a finishing pig, which has a body weight more than 60 Kg, the daily amount of the animal feed is 25 to 42 g/Kg body weight.

The present disclosure also provides a method for improving pork quality, comprising administering to a pig the composition described above.

The disclosure will be further described by way of the following examples. However, it should be understood that the following examples are solely intended for the purpose of illustration and should not be construed as limiting the disclosure in practice.

EXAMPLES

General Experimental Materials:
1. *Lactobacillus plantarum* LP28

*Lactobacillus plantarum* LP28, which is disclosed in the applicants' previous U.S. Patent Application Publication No. 2011/0052553 A1, has been deposited at the China General Microbiological Culture Collection Center (CGMCC) (Institute of Microbiology, Chinese Academy of Sciences, No. 1 West Beichen Road, Chaoyang District, Beijing 100101, China) under an accession number CGMCC 3346 since Oct. 19, 2009.

2. *Streptococcus thermophilus* ST30

*Streptococcus thermophilus* ST30 has been deposited at Deutsche Sammlung von Mikroorganismen und Zellkulturen GmbH (Inhoffenstr. 7B, D-38124 Braunschweig, Germany) under an accession number DSM 32788 since Apr. 3, 2018.

General Procedures:
1. Statistical Analysis

All the experiments described below were performed in triplicate. Statistical analysis was conducted using SPSS statistics software (version 18.0). The experimental data were expressed as mean±SD (standard deviation) and were analyzed using Mann-Whitney U test so as to assess the difference between the groups. Statistical significance is indicated by p<0.05.

Example 1. Preparation of LAB Composition of Present Disclosure

A seed medium was prepared using the recipe shown in Table 1. A respective one of *Lactobacillus plantarum* LP28 and *Streptococcus thermophilus* ST30 was inoculated in an amount of 3% (v/v) into 3 L of the seed medium, and was then cultured at 37° C. for 18 hours. The respective resultant culture was poured into 150 L of the seed media and was further cultured at 37° C. for 16 hours.

TABLE 1

| Ingredients | Concentration (g/L) |
| --- | --- |
| Glucose | 25 |
| Skim milk powder | 15 |
| Tween-80 | 1 |
| Yeast extract | 20 |
| $MnSO_4$ | 0.05 |
| $K_2HPO_4$ | 3 |

The balance is distilled water.

After centrifugation at 12,000 rpm and 4° C. for 30 minutes, the resultant cell pellet was collected, followed by freeze-drying, so as to obtain a respective one of the following: a freeze-dried powder of *Lactobacillus plantarum* LP28 having a bacterial concentration of $10^{11}$ to $10^{12}$ CFU/g and a freeze-dried powder of *Streptococcus thermophilus* ST30 having a bacterial concentration of $10^{10}$ to $10^{11}$ CFU/g. The freeze-dried powder of *Lactobacillus plantarum* LP28 and the freeze-dried powder of *Streptococcus thermophilus* ST30 were mixed in a weight ratio of 1.8:1, and the resultant LAB composition was used for the following example.

Example 2. Evaluation for the Effect of LAB Composition on Improving Pork Quality Materials and Methods:
A. Test Animals Commercial LYD (Landrace, Yorkshire, and Duroc) three-breed cross piglets (at the age of 28 days and having a weight of 7 kg) were purchased from the SHANG-YONG Farm, Taiwan. The piglets were kept in a pigsty with natural light and a temperature of 25-32° C., and diet and water were sufficient and accessible to the piglets at all times. All animal experiments were conducted according to guidelines of Animal Care Committee of the Council of Agriculture, Taiwan.

B. Preparation of Feed Containing LAB Composition of Present Disclosure

The LAB composition obtained in Example 1 and maltodextrin were mixed in a weight ratio of 6:94, so as to obtain a feed additive having a bacterial concentration of 109 CFU/g for *Lactobacillus plantarum* LP28 and a bacterial concentration of $10^8$ CFU/g for *Streptococcus thermophilus* ST30. The resultant feed additive and a basal diet (Jie Sheng Co., Ltd., Taiwan) were mixed in a weight ratio of 1:5000, so as to obtain a probiotic feed. In addition, 200 mg of amoxicillin (Yung Shin Pharm Ind Co., Ltd., Taiwan) and 250 mg of thiamphenicol (Yung Shin Pharm Ind Co., Ltd., Taiwan) were added to 1 kg of a basal diet, so as to obtain an antibiotic feed.

C. Feeding with Feed Containing LAB Composition of Present Disclosure

The piglets were divided into a control group (n=20) and an experimental group (n=20), wherein the control group was fed with the antibiotic feed prepared in section B of this example, and the experimental group was fed with the probiotic feed prepared in section B of this example. Each piglet was fed two times a day for a total period of 154 days.

After feeding for 154 days, each piglet was slaughtered and carved according to Requirements for Slaughter Operation, Taiwan. The longissimus dorsi, boston butt, picnic shoulder, ham, short loin, short fillet, and belly were obtained from each pig carcass and were used for the following evaluation of pork quality.

D. Evaluation of Pork Quality

In order to evaluate the quality of pork samples obtained in section C of this example, the following experiments were conducted.

D-1. Determination of Carcass Parameters

The loin eye area, loin weight, fat percentage, lean percentage, and marbling of the pork samples were determined according to Guidelines of National Pork Producers Council and using a method that was slightly modified from that described by Huff-Lonergan E. et al. (2002), *J. Anim. Sci.*, 80:617-627. Specifically, the longissimus dorsi was used to conduct the analyses of the loin eye area and loin weight, and the boston butt, picnic shoulder, ham, short loin, short fillet, and belly were used to conduct the analyses of the fat percentage and lean percentage.

The distribution of marbling in longissimus dorsi was assessed visually by scoring on a scale from 1 to 5 (the higher scale indicated the higher intramuscular fat).

In addition, Hunter L and a values of the cross section of longissimus dorsi near the $11^{th}$-rib region were measured by a Color and Color Difference Meter TC-1 (Tokyo Denshoku Co., Ltd.). The higher Hunter L values indicated the higher lightness of the pork. The higher Hunter a values indicated the higher redness of the pork.

For evaluation of the firmness and toughness, the longissimus dorsi was packaged in aluminium foil and then sealed with a ziplock bag. Thereafter, the ziplock bag was heated at 80° C. in a water bath for 30 minutes, and the longissimus dorsi thus cooked was cut into a cuboid of 3 cm×1 cm×1 cm, followed by detecting firmness and toughness using a Texture Analyzer (TA-XT Plus™, Stable Micro Systems Co., Ltd.).

D-2. Analysis of Sensory Characteristics

The sensory characteristics of the longissimus dorsi were analyzed using a method that was slightly modified from that described by Huff-Lonergan E. et al. (2002), supra. The sensory characteristics included color, flavor, juiciness, tenderness, and total acceptability, and these five characteristics were recorded by consumers and quantified by scoring on a scale from 1 to 7. The higher scale indicated the higher quality of the pork (i.e. scale 1 indicated the worst color, worst flavor, least juiciness, least rigidness, and most unacceptableness in the viewpoint of the consumers; scale 7 indicated the best color, best flavor, most juiciness, most tenderness, and most preference in the viewpoint of the consumers).

The data obtained in subsections D-1 and D-2 were subjected to statistical analysis according to the method described in section 1 of General Procedures.

Results:

The carcass parameters determined are shown in Table 2. It can be seen from Table 2 that the marbling of the experimental group was significantly higher than that of the control group, and the firmness of the experimental group was significantly lower than that of the control group. Furthermore, the Hunter L and a values of the experimental group were higher than those of the control group.

TABLE 2

| Items analyzed | Control group | Experimental group |
| --- | --- | --- |
| Fat percentage (%) | 19.43 ± 4.40 | 18.98 ± 3.09 |
| Lean percentage (%) | 54.42 ± 4.48 | 55.82 ± 2.25 |
| Loin eye area ($cm^2$) | 74.24 ± 5.60 | 81.51 ± 9.25 |
| Loin weight (kg) | 3.28 ± 0.31 | 3.44 ± 0.30 |
| Marbling | 2.26 ± 0.42 | 3.08 ± 0.24* |
| Firmness (kg) | 9.99 ± 1.99 | 6.56 ± 2.15* |
| Toughness (kg · sec) | 18.14 ± 5.43 | 10.98 ± 3.96 |
| Hunter L value | 39.89 ± 1.42 | 44.50 ± 8.11 |
| Hunter a value | 4.71 ± 1.13 | 6.96 ± 1.79 |

The symbol "*" represents $p < 0.05$ (compared with the control group).

The score results of the analysis of sensory characteristics are shown in Table 3. It can be seen from Table 3 that the color score of the experimental group was significantly higher than that of the control group. Furthermore, the tenderness score of the experimental group was higher than that of the control group.

TABLE 3

| Items analyzed | Control group | Experimental group |
| --- | --- | --- |
| Color | 4.00 ± 0.77 | 4.47 ± 1.25* |
| Flavor | 4.07 ± 1.27 | 4.22 ± 1.35 |
| Juiciness | 3.56 ± 1.20 | 3.93 ± 1.32 |
| Tenderness | 3.36 ± 1.17 | 3.78 ± 1.40 |
| Total acceptability | 4.47 ± 1.06 | 4.56 ± 1.14 |

The symbol "*" represents $p < 0.05$ (compared with the control group).

Summarizing the above test results, it is clear that the LAB composition of present disclosure is effective in upgrading color, tenderness, and marbling of the pork, and hence can be used as a feed additive for improving pork quality.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for improving pork marbling, comprising:
   administering to a pig an animal feed containing a basal diet and a composition including *Lactobacillus plantarum* LP28 and *Streptococcus thermophilus* ST30, wherein *Lactobacillus plantarum* LP28 is deposited at the China General Microbiological Culture Collection Center (CGMCC) under an accession number CGMCC 3346, and *Streptococcus thermophilus* ST30 is deposited at Deutsche Sammlung von Mikroorganismen and Zellkulturen GmbH under an accession number DSM 32788, and a weight ratio of the composition and the basal diet ranges from 1:2000 to 1:10000.

2. The method of claim 1, wherein the weight ratio of the composition and the basal diet is 1:5000.

3. The method of claim 1, wherein in the composition, *Lactobacillus plantarum* LP28 and *Streptococcus thermophilus* ST30 are present in the form of freeze-dried powders.

4. The method of claim 1, wherein in the composition, *Lactobacillus plantarum* LP28 and *Streptococcus thermophilus* ST30 are present in a weight ratio ranging from 1:1 to 1.8:1.

* * * * *